(12) United States Patent
Sugiura

(10) Patent No.: US 7,587,232 B2
(45) Date of Patent: Sep. 8, 2009

(54) MAGNETIC RESONANCE IMAGING APPARATUS, MAGNETIC RESONANCE DATA PROCESSING APPARATUS, MAGNETIC RESONANCE DATA PROCESSING PROGRAM AND MAGNETIC RESONANCE IMAGING APPARATUS CONTROL METHOD

(75) Inventor: Satoshi Sugiura, Otawara (JP)

(73) Assignees: Kabushiki Kaisha Toshiba, Minato-Ku, Tokyo (JP); Toshiba Medical Systems Corporation, Otawara-Shi, Tochigi (JP)

( * ) Notice: Subject to any disclaimer, the term of this patent is extended or adjusted under 35 U.S.C. 154(b) by 50 days.

(21) Appl. No.: 11/362,724

(22) Filed: Feb. 28, 2006

(65) Prior Publication Data

US 2007/0203412 A1    Aug. 30, 2007

(51) Int. Cl.
 A61B 5/05   (2006.01)
 G01V 3/00   (2006.01)

(52) U.S. Cl. ...................... 600/410; 324/307

(58) Field of Classification Search ............ 600/410
See application file for complete search history.

(56) References Cited

U.S. PATENT DOCUMENTS

| | | | | |
|---|---|---|---|---|
| 4,797,615 A * | 1/1989 | Rotem et al. | ............... | 324/309 |
| 5,669,382 A * | 9/1997 | Curwen et al. | ............. | 600/425 |
| 5,803,914 A * | 9/1998 | Ryals et al. | ................ | 600/407 |
| 6,389,310 B1 * | 5/2002 | Demonceau et al. | ........ | 600/512 |
| 7,031,504 B1 * | 4/2006 | Argiro et al. | ............... | 382/131 |
| 7,127,093 B2 * | 10/2006 | Bansal et al. | ............... | 382/128 |
| 7,233,818 B1 * | 6/2007 | Aletras et al. | ............... | 600/410 |
| 2002/0032376 A1 * | 3/2002 | Miyazaki et al. | ........... | 600/410 |
| 2003/0053667 A1 * | 3/2003 | Paragios et al. | ............ | 382/128 |
| 2003/0171671 A1 * | 9/2003 | Miyazaki | .................... | 600/420 |
| 2004/0068175 A1 * | 4/2004 | Miyazaki et al. | ........... | 600/410 |
| 2004/0132006 A1 * | 7/2004 | O'Donnell et al. | ............ | 435/4 |
| 2004/0258285 A1 * | 12/2004 | Hansen et al. | ............. | 382/128 |
| 2006/0013482 A1 * | 1/2006 | Dawant et al. | ............. | 382/173 |
| 2006/0052690 A1 * | 3/2006 | Sirohey et al. | ............. | 600/420 |
| 2006/0155185 A1 * | 7/2006 | Breeuwer | .................. | 600/407 |
| 2006/0161060 A1 * | 7/2006 | Pai | ............................. | 600/431 |
| 2007/0135705 A1 * | 6/2007 | Lorenz et al. | ............... | 600/410 |

OTHER PUBLICATIONS

Ding et al., *Improved Coverage in Dynamic Contrast-Enhanced Cardiac MRI Using Interleaved Gradient-Echo EPI*, Magnetic Resonance in Medicine, 39:514-519 (1998).

(Continued)

*Primary Examiner*—Eric F Winakur
*Assistant Examiner*—Helene Bor
(74) *Attorney, Agent, or Firm*—Nixon & Vanderhye PC

(57) ABSTRACT

Image reconstruction is executed by using magnetic resonance signals obtained by asynchronous multi-slice dynamic imaging without using any ECG-gated technique to obtain a plurality of MR images for each time phase with respect to a plurality of cross-sections corresponding to sequential changes in radio-frequency pulse frequency. The heart of a subject to be examined in MR images in the same time phase is developed by being divided into a plurality of small regions, and a developed view representing the average value of pixel values in each of the small regions is generated. For example, the developed views in the respective time phases are continuously displayed in a time-series manner.

20 Claims, 9 Drawing Sheets

OTHER PUBLICATIONS

Slavin et al., *First-Pass Myocardial Perfusion MR Imaging with Interleaved Notched Saturation Feasibility Study*, Radiology, 219:258-263, 2001.

Jerosch-Herold et al., *Analysis of Myocardial Perfusion MRI*, Journal of Magnetic Resonance Imaging, 19:758-770 (2004).

Sakuma et al., *Diagnosis of ischemic heart disease using contrast enhanced MR*, Innervision (15.13) 2000, pp. 59-60, Nov. 25, 2000, in Japanese.

Nanjo et al., *Evaluation of myocardial perfusion and viability*, Innervision (17.9) 2002, pp. 10-13, Aug. 25, 2002, in Japanese.

*The key for anatomy and physiology in cardiovascular magnetic resonance imaging*, Innervision (17.9) 2002, pp. 1-4, in Japanese.

\* cited by examiner

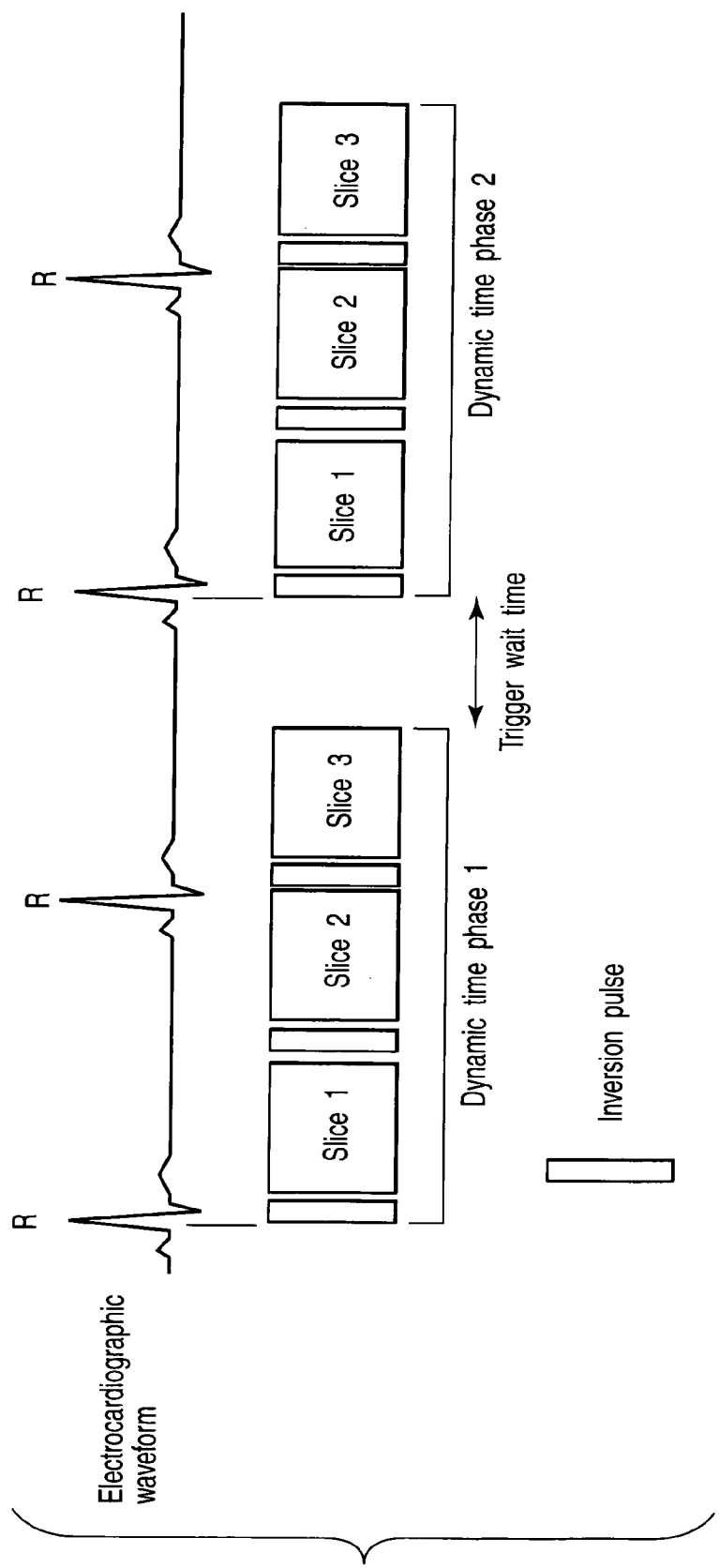
F I G. 3

MAGNETIC RESONANCE IMAGING APPARATUS, MAGNETIC RESONANCE DATA PROCESSING APPARATUS, MAGNETIC RESONANCE DATA PROCESSING PROGRAM AND MAGNETIC RESONANCE IMAGING APPARATUS CONTROL METHOD

BACKGROUND OF THE INVENTION

1. Field of the Invention

A magnetic resonance imaging apparatus is an apparatus which images the chemical and physical microscopic information of a substance or observes a chemical shift spectrum by using a phenomenon in which when a group of nuclei having a unique magnetic moment is placed in a uniform static field, they resonantly absorb the energy of a radio-frequency magnetic field that rotates at a specific frequency.

2. Description of the Related Art

In diagnosis of ischemic heart disease, as a method of evaluating myocardial hemodynamics using a magnetic resonance imaging apparatus, there is available a method (myocardial perfusion) of observing the process of imaging the cardiac muscle with a contrast medium by injecting the contrast medium through a vein and performing left ventricular short-axis multislice contrast-enhanced T1-weighted imaging together with an ECG-gated technique during the first circulation. The result obtained by this myocardial perfusion is evaluated by continuously displaying (cine-displaying) the respective slices in the time direction or by dividing each left ventricular short-axis slice into a plurality of radial regions, converting various measurement values obtained from graphs (dynamic curves) representing temporal changes in signal values in the respective divided regions into developed views, i.e., so-called Bull's eye images, in which the measurement values are concentrically arranged from the cardiac base to the cardiac apex in correspondence with a color map or gray scale, and displaying the image, as described in, for example, Sakuma et al., "Diagnosis of Ischemic Heart Disease by Contrast Medium MRI", INNERVISION (15.13) 2000, pp. 59-66, Nanjou et al., "Myocardial Perfusion/Evaluation of Cardiac Muscle Viability", INNERVISION (17.9) 2002, pp. 10-14, and Fujimoto et al., "Points of Anatomical/Physiological Function Necessary for MRI in Cardiovascular Region", INNERVISION (17.9) 2002, pp. 1-4.

In order to obtain an electrocardiographic waveform, it takes a lot of trouble to attach electrodes for electrocardiographic signal detection to a subject to be examined before examination. In addition, depending on patients, in order to obtain a proper electrocardiographic signal, it takes much time to, for example, re-position the electrodes. Furthermore, noise caused by gradient field switching for magnetic resonance imaging may be induced into an electrocardiographic waveform. As a result, proper synchronization may not be established, and imaging operation cannot be performed or image quality may deteriorate.

In addition, since a radio-frequency pulse for magnetic resonance imaging is applied while the electrodes are attached to the subject, the radio-frequency pulse is induced into the loop formed by the electrodes, a wire for transferring an electrocardiographic waveform, and the human body. This may cause a burn. This risk increases in high magnetic field MRI with high radio-frequency pulse power.

In addition, since conventional moving image display is performed for each slice, it is difficult to observe the state of blood supply in the entire cardiac muscle at a glance.

BRIEF SUMMARY OF THE INVENTION

The present invention has been made in consideration of the above situation, and has as its object to provide a magnetic resonance imaging apparatus, magnetic resonance data processing apparatus, magnetic resonance imaging apparatus control method and magnetic resonance data processing method which can provide information of myocardial hemodynamics without using any electrocardiographic signals.

According to an aspect of the present invention, there is provided a magnetic resonance imaging apparatus which comprises: an imaging unit which executes an imaging operation of repeatedly applying a gradient field and a radio frequency pulse to a subject to be examined which is placed in a static field space and receiving a magnetic resonance signal generated in the heart of the subject by application of the gradient field and the radio frequency pulse; a control unit which controls the imaging unit so as to sequentially change a frequency of the radio frequency pulse in each application of the gradient field and the radio frequency pulse; an image reconstruction unit which executes image reconstruction by using the magnetic resonance signal received by the imaging operation and obtains a plurality of first images for each time phase with respect to a plurality of cross sections corresponding to sequential changes in the frequency of the radio frequency pulse; an image generating unit which divides the heart of the subject in the first images in the same time phase into a plurality of small regions and generates a first developed view representing a specific value of pixel values in the each small region obtained for each time phase; and a display unit which displays the first developed view for each time phase in a predetermined form.

According to another aspect of the present invention, there is provided a magnetic resonance data processing apparatus which comprises: a storage unit which stores magnetic resonance data obtained by acquiring magnetic resonance signals generated in the heart of a subject to be examined by imaging operation based on a pulse sequence of repeatedly applying a gradient field and a radio-frequency pulse to the subject placed in a static field space and sequentially changing a frequency of the radio-frequency pulse; an image reconstruction unit which executes image reconstruction by using the magnetic resonance data and obtains a plurality of first images for each time phase with respect to a plurality of cross-sections corresponding to sequential changes in the frequency of the radio-frequency pulse; an image generating unit which generates a first developed view representing a specific value of pixel values in said each small region obtained when the heart of the subject in the first images in the same time phase is developed by being divided into a plurality of small regions; and a display unit which displays the first developed view for each time phase in a predetermined form.

According to yet another aspect of the present invention, there is provided a magnetic resonance imaging apparatus control method which comprises: executing image reconstruction using magnetic resonance data obtained by acquiring magnetic resonance signals generated in the heart of a subject to be examined by performing imaging operation based on a pulse sequence of repeatedly applying a gradient field and a radio-frequency pulse to the subject placed in a static field space and sequentially changing a frequency of the radio-frequency pulse, thereby obtaining a plurality of first images for each time phase with respect to a plurality of cross-sections corresponding to sequential changes in the frequency of the radio-frequency pulse; dividing the heart of the subject in the first images in the same time phase into a plurality of small regions and generating a first developed view representing a specific value of pixel values in the each small region obtained for each time phase; and a display unit which displays the first developed view for each time phase in a predetermined form.

According to yet another aspect of the present invention, there is provided a magnetic resonance imaging apparatus control method which comprises: executing image reconstruction using magnetic resonance data obtained by acquiring magnetic resonance signals generated in the heart of a subject to be examined by performing imaging operation based on a pulse sequence of repeatedly applying a gradient field and a radio-frequency pulse to the subject placed in a static field space and sequentially changing a frequency of the radio-frequency pulse, thereby obtaining a plurality of first images for each time phase with respect to a plurality of cross-sections corresponding to sequential changes in the frequency of the radio-frequency pulse; and dividing the heart of the subject in the first images in the same time phase into a plurality of small regions and generating a first developed view representing a specific value of pixel values in the each small region obtained for each time phase; and a display unit which displays the first developed view for each time phase in a predetermined form.

According to yet another aspect of the present invention, there is provided a magnetic resonance imaging apparatus control method which comprises: an imaging unit which executes imaging operation of repeatedly applying a gradient field and a radio-frequency pulse to a subject to be examined which is placed in a static field space and receiving a magnetic resonance signal generated in the heart of the subject by application of the gradient field and the radio-frequency pulse; a control unit which controls the imaging unit so as to sequentially change a frequency of the radio-frequency pulse in each application of the gradient field and the radio-frequency pulse; an image reconstruction unit which executes image reconstruction by using the magnetic resonance signal received by the imaging operation and obtains a plurality of first images for each time phase with respect to a plurality of cross-sections corresponding to sequential changes in the frequency of the radio-frequency pulse; an image generating unit which divides the heart of the subject in the first images in the same time phase into a plurality of small regions and generates a first developed view representing an average value of pixel values in the each small region or a median value of pixel values in the each small region for each time phase; and a display unit which displays the first developed view for each time phase in a predetermined form.

BRIEF DESCRIPTION OF THE SEVERAL VIEWS OF THE DRAWING

FIG. 3 is a view for explaining a data acquisition method based on ECG-gated myocardial perfusion imaging;

DETAILED DESCRIPTION OF THE INVENTION

Figure 1:
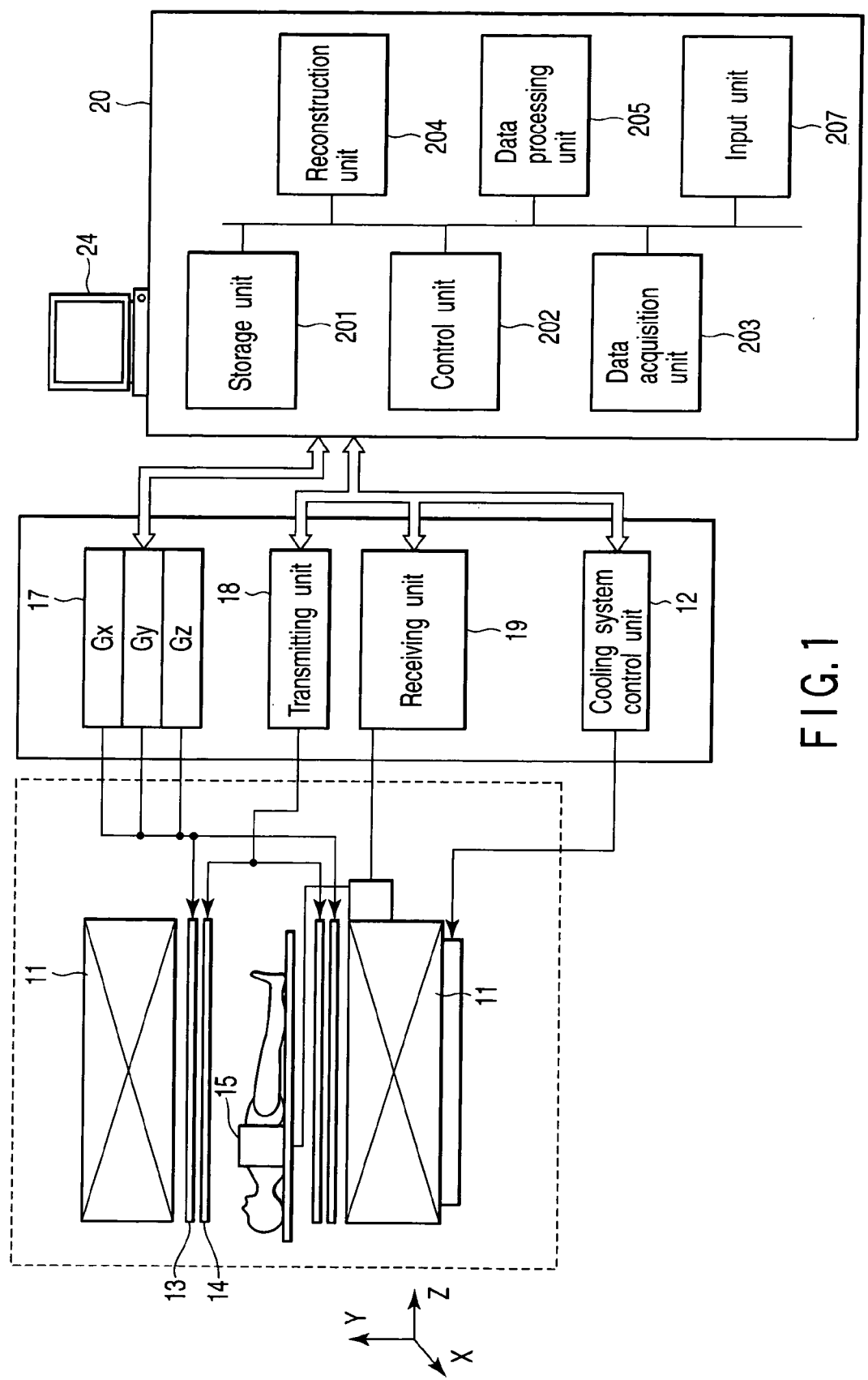
FIG. 1 is a block diagram showing the arrangement of a magnetic resonance imaging apparatus according to this embodiment.

An embodiment of the present invention will be described below with reference to the views of the accompanying drawing. Note that the same reference numerals in the following description denote constituent elements having substantially the same functions and arrangements, and a repetitive description will be made only when required.

FIG. 1 is a block diagram showing the arrangement of a magnetic resonance imaging apparatus according to this embodiment. As shown in FIG. 1, the magnetic resonance imaging apparatus comprises a static field magnet 11, cooling system control unit 12, gradient field coil 13, radio frequency transmission coil 14, gradient field coil device power supply 17, transmitting unit 18, receiving unit 19, computer system 20, and display 24.

The static field magnet 11 is a magnet which generates a static field having a placement space in which a subject to be examined is placed. The static field magnet 11 forms a uniform static field in the placement space.

The cooling system control unit 12 controls the cooling mechanism of the static field magnet 11.

The gradient field coil 13 is provided inside the static field magnet 11 and is shorter than the static field magnet 11. The gradient field coil 13 converts pulse currents supplied from the gradient field coil device power supply 17 into gradient fields. A signal generation region (position) is specified by the gradient fields generated by the gradient field coil 13.

Assume that in this embodiment, the gradient field coil 13 and the static field magnet 11 have cylindrical shapes.

The radio-frequency transmission coil (RF transmission coil) 14 is a coil for applying radio-frequency pulses to an imaging region of a subject to be examined to generate magnetic resonance signals. The radio-frequency transmission coil 14 is a whole-body RF coil, which can also be used as a reception coil when, for example, an abdominal region or the like is to be imaged.

A radio-frequency reception coil (RF reception coil) 15 is a coil which is placed near the subject, and preferably in contact with, the subject so as to hold it, and receives magnetic resonance signals from the subject. In general, the radio-frequency reception coil 15 has a shape specialized for each region.

Note that FIG. 1 exemplifies a cross-coil system comprising a radio-frequency transmission coil and a radio-frequency reception coil as discrete components. However, the present invention may use a single coil system having one coil having these functions.

The gradient field coil device power supply 17 generates a pulse current for forming a gradient field and supplies the current to the gradient field coil 13. The gradient field coil device power supply 17 controls the polarity of a gradient filed by switching the direction of a pulse current supplied to the gradient field coil 13 under the control of a control unit 202 (to be described later).

The transmitting unit 18 has an oscillating unit, phase selecting unit, frequency conversion unit, amplitude modulating unit, and radio-frequency power amplifying unit (none of which are shown), and transmits radio-frequency pulses corresponding to a Larmor frequency to the radio-frequency coil for transmission. The magnetization of a predetermined nucleus of the subject is excited by the radio-frequency wave generated from the radio-frequency transmission coil 14 upon this transmission.

The receiving unit 19 has an amplifying unit, intermediate frequency conversion unit, phase detecting unit, filter, and A/D converter (none of which are shown). The receiving unit 19 performs amplification processing, intermediate frequency conversion processing using an oscillation frequency, phase detection processing, filter processing, and A/D conversion processing for the magnetic resonance signal (radio-frequency signal) which is emitted when the magnetization of the nucleus relaxes from the excited state to the ground state and is received from the radio-frequency reception coil 15.

The computer system 20 has a storage unit 201, the control unit 202, a data acquisition unit 203, a reconstruction unit 204, a data processing unit 205, and an input unit 207.

The storage unit 201 stores magnetic resonance signal data (raw data) before reconstruction which is obtained through the receiving unit 19, magnetic resonance image data reconstructed by the reconstruction unit 204, and the like for each patient. The storage unit 201 stores imaging programs for the execution of imaging sequences corresponding to various kinds of imaging methods.

The control unit 202 has a CPU, a memory, and the like (none of which are shown), and serves as a control center for the overall system to statically or dynamically control this magnetic resonance imaging apparatus. For example, the control unit 202 reads out an imaging program corresponding to the imaging method selected through the input unit 207 from the storage unit 201, and executes control on the overall apparatus in accordance with the program.

The data acquisition unit 203 acquires the digital signals (magnetic resonance signals) sampled by the receiving unit 19.

The reconstruction unit 204 executes post-processing, i.e., reconstruction such as a Fourier transform, for the data acquired by the data acquisition unit 203 to obtain the spectrum data or image data of a desired nuclear spin inside the subject.

The data processing unit 205 executes the generation of a Bull's eye image based on a plurality of dynamic images in the same time phase, the generation of a dynamic curve, the generation of a Bull's eye image based on the dynamic curve, and the like in asynchronous myocardial perfusion imaging (to be described later). These processes will be described in detail later.

The display 24 is an output unit which displays the spectrum data, image data, or the like input from the computer system 20.

ECG-Gated Myocardial Perfusion Imaging

A general ECG gated myocardial perfusion imaging technique will be described first for comparison with asynchronous myocardial perfusion imaging (to be described later) executed by the magnetic resonance imaging apparatus.

Figure 2:
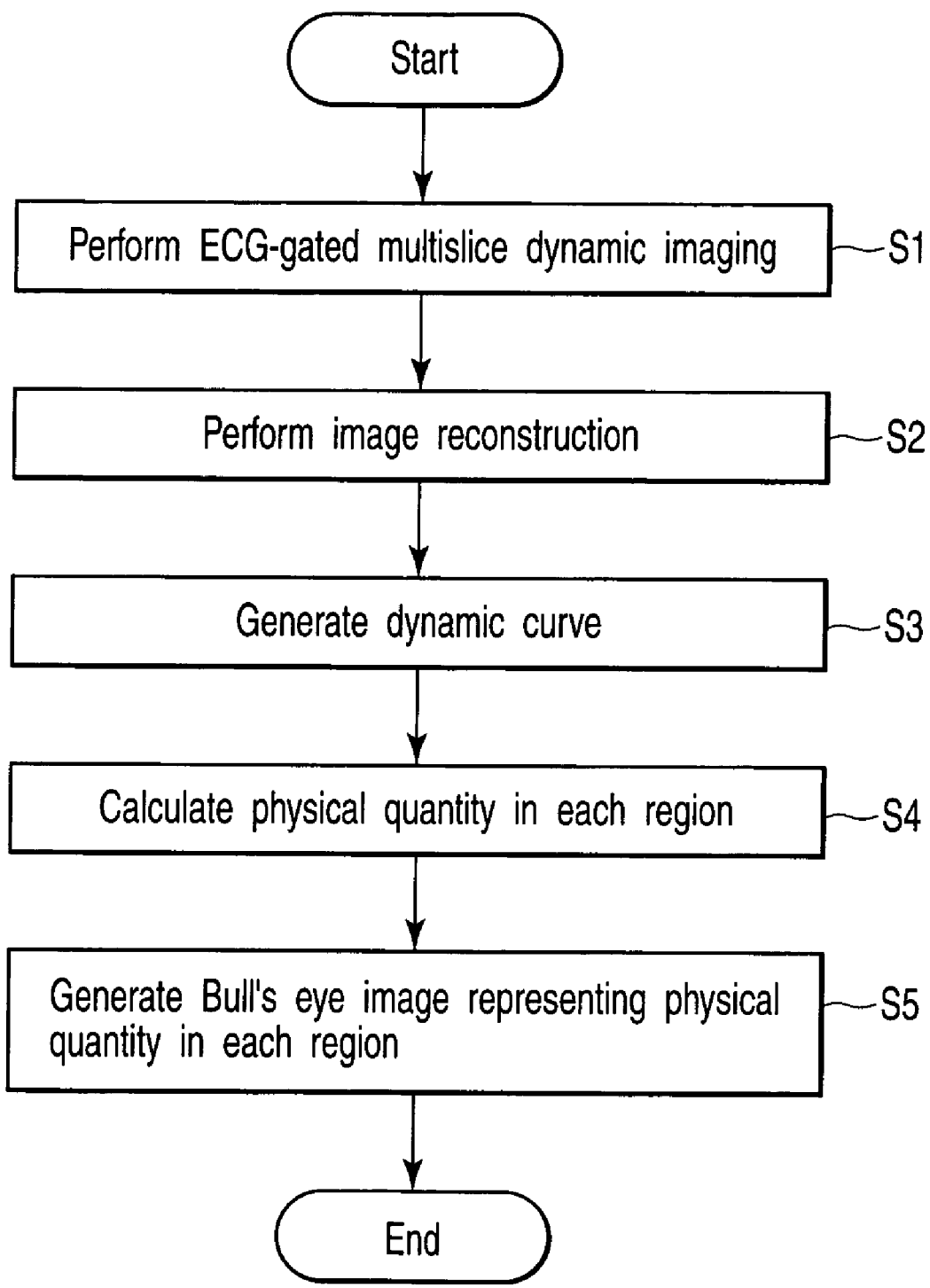
FIG. 2 is a flowchart showing the flow of each process to be executed in ECG-gated myocardial perfusion imaging.

FIG. 2 is a flowchart showing the flow of each process to be executed in ECG-gated myocardial perfusion imaging. As shown in FIG. 2, in this imaging technique, a contrast medium is bolus-injected through a vein first, and then data of the state of the first circulation is acquired by performing dynamic (continuous) imaging together with an ECG-gated technique with respect to a plurality of left ventricular short-axis slices by using a pulse sequence which can obtain contrast-enhanced T1-weighted images, e.g., a fast field echo method or an EPI method (step S1). Note that in the following description, when multi slice scans are repeated with a same time-interval or different time-intervals, a period in which one multi slice scan executed will be referred to as a "dynamic time phase".

FIG. 3 is a view for explaining a data acquisition method based on ECG-gated myocardial perfusion imaging. This exemplifies a case wherein the data of three slices are acquired per two heartbeats, and this operation is repeated in the first circulation. Note that an inversion pulse for T1 contrast is applied immediately before the data acquisition of each slice. The data acquired in this manner are reconstructed into an MR image of each cross-section (step S2).

Figure 4:
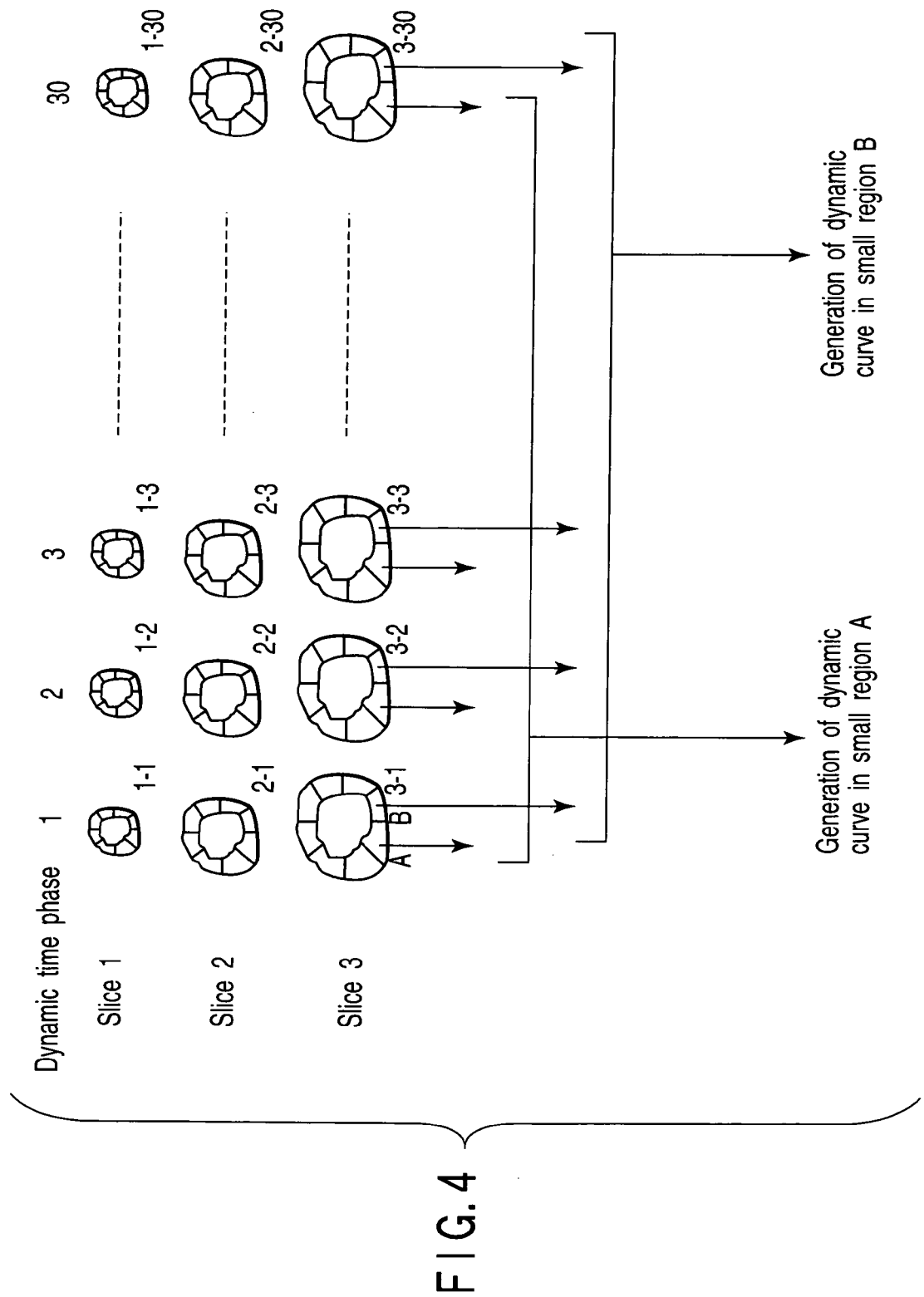
FIG. 4 is a view showing cross-sections (slices 1, 2, and 3) obtained in the respective dynamic time phases in accordance with the scan sequence shown in FIG. 3.

FIG. 4 is a view showing MR images (slices 1, 2, 3) of cross-sections obtained in the respective dynamic time phases by the data acquisition method shown in FIG. 3. Referring to FIG. 4, reference numerals 1-1, 2-1, 3-1, 1-2, 2-2, 3-2, . . . , 1-30, 2-30, and 3-30 denote MR images acquired by this technique. FIG. 4 shows an example of a total of three cross-sections, i.e., slices 1, 2, and 3, in the direction from the cardiac apex to the cardiac base, with a dynamic time phase count of 30.

Note that cine display of each of the obtained MR images can also be performed at a corresponding slice position (continuous moving image display in the time direction, e.g., continuous display in the order of 1-1, 1-2, and 1-3 in FIG. 3).

Subsequently, the cardiac muscle on each MR image is divided into a plurality of small regions, and a dynamic curve (a graph representing temporal changes in pixel value) is generated on the basis of the average pixel value in each region (step S3).

Figure 5:
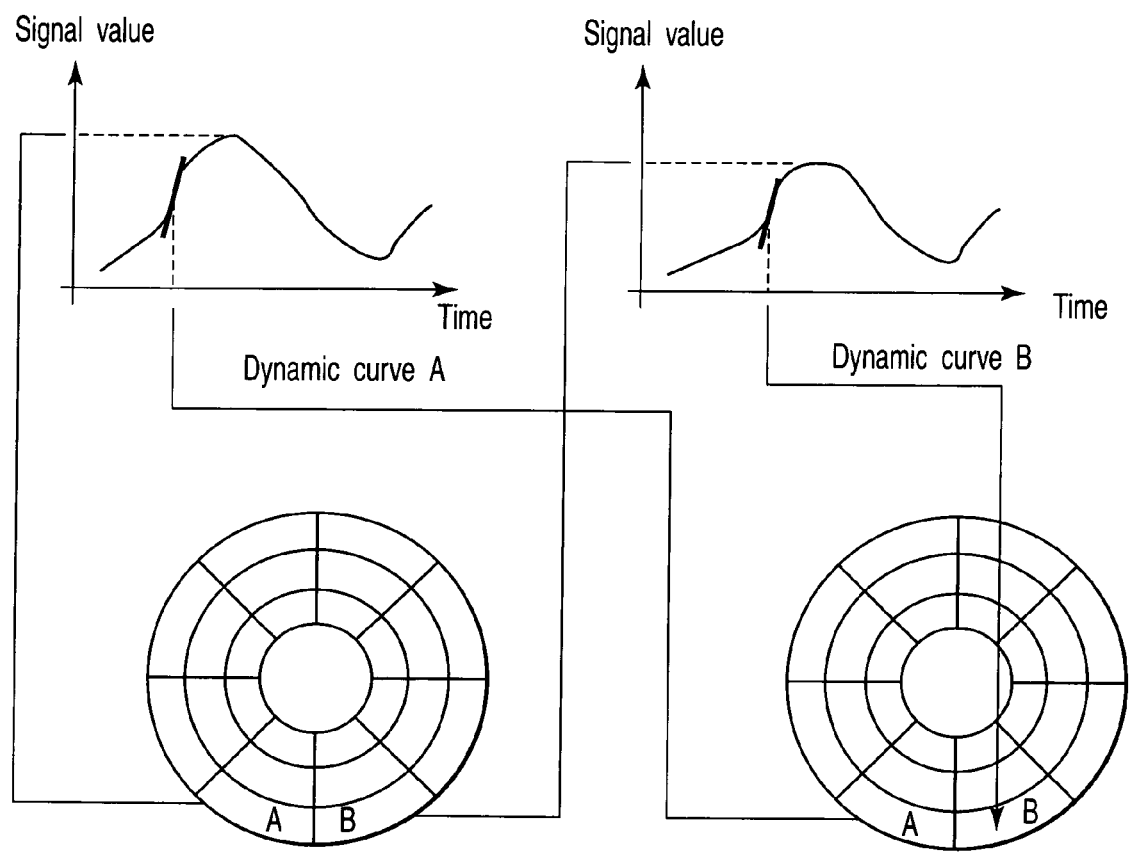
FIG. 5 is a view showing, on the upper side, a dynamic curve (left) in a small region A and a dynamic curve (right) in a small region B, and showing, on the lower side, a Bull's eye image (left) concerning the small region A and a Bull's eye image (right) concerning the small region B.

That is, an endocardial and an epicardial contour are extracted from each MR image in FIG. 3, and the region between the two portions is divided into 100 radial regions (for the sake of simplicity, FIG. 5 shows a case wherein the region is divided into eight small regions, and the entire left ventricular cardiac muscle is divided into 3×8=24 small regions). The average values of the pixel values in the respective regions are obtained, and are time-serially plotted, thereby forming a dynamic curve for each small region. Consider, for example, a small region A. The averages of the pixel values in the small region A in the respective dynamic time phases are calculated, and the respective average values of images 3-1 to 3-30 in the small region A are time-serially plotted to generate a dynamic curve. Note that the upper part of FIG. 5 shows a dynamic curve (left) concerning the small region A, and a dynamic curve (right) concerning a small region B.

Parameter values (characteristic values) representing temporal change characteristics such as a maximum signal value, a maximum gradient, the time taken to reach the maximum gradient, and an average signal value for each small region are calculated on the basis of each dynamic curve (step S4). The obtained parameter values (the two values, i.e., the maximum signal value and the time taken to reach the maximum gradient) are mapped in the corresponding regions of the concentric circles representing the entire left ventricular cardiac muscle in correspondence with colors or grayscale values, thereby generating an image for each dynamic time phase. This image is obtained by developing a subject to be imaged (the left ventricular cardiac muscle in this case) into 24 small divided regions in the form of concentric circles, and is called a "developed view" or "Bull's eye image" owing to its form. This display method, i.e., the development display, is called Bull's eye display. These images and their display method are generally used in other diagnosis methods such as nuclear medicine examination, and are used for the evaluation of a blood flow distribution in each cardiac muscle region.

The lower part of FIG. 5 shows the Bull's eye image (left) concerning the small region A and the Bull's eye image (right) concerning the small region B. Referring to FIG. 5, the inside and outside of the concentric circles correspond to the cardiac apex and the cardiac base, respectively.

Asynchronous Myocardial Perfusion Imaging

The asynchronous myocardial perfusion imaging technique executed by the magnetic resonance imaging apparatus will be described next. This imaging technique provides a myocardial perfusion image data acquisition method which does not require any ECG gated technique, a post processing method, and a display method.

Figure 6:
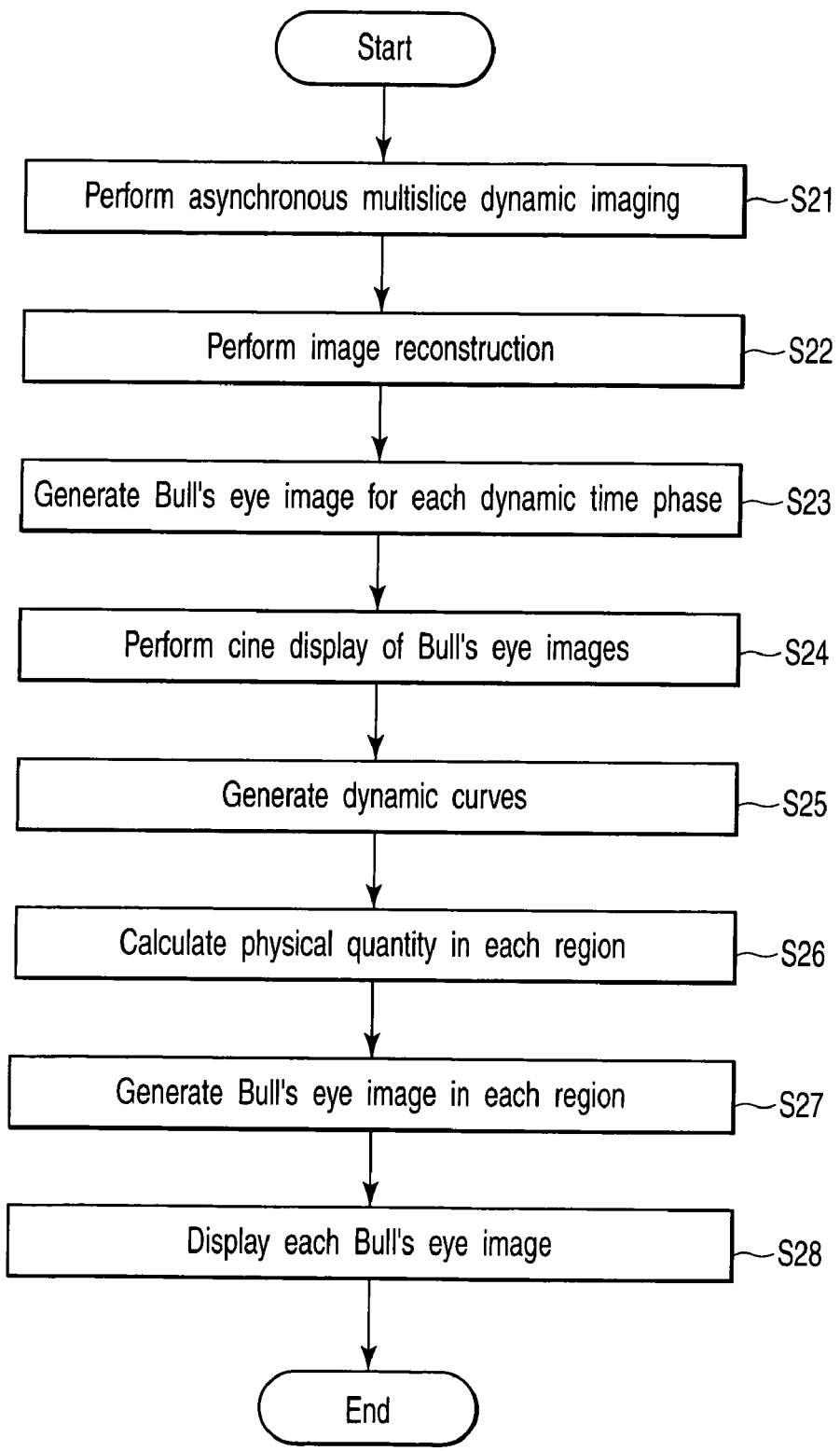
FIG. 6 is a flowchart showing the flow of each process to be executed in asynchronous myocardial perfusion imaging.

FIG. 6 is a flowchart showing the flow of each process executed in asynchronous myocardial perfusion imaging. As shown in FIG. 6, in this imaging technique, data acquisition can be executed by multislice dynamic imaging without requiring any ECG-gated technique (asynchronous) (step S21).

Figure 7:
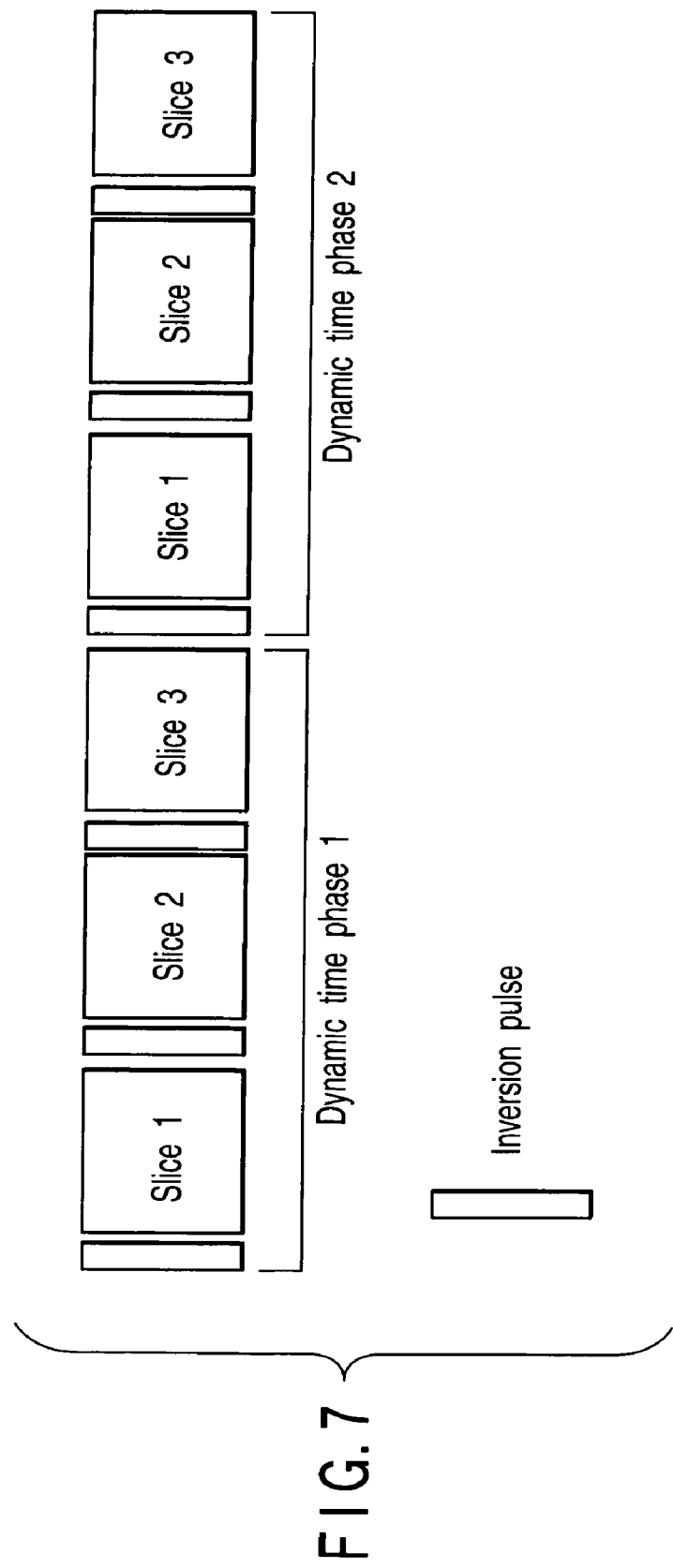
FIG. 7 is a view showing an example of a scan sequence executed in asynchronous myocardial perfusion imaging.

FIG. 7 is a view showing an example of a scan sequence executed in this imaging technique. A pulse sequence used for data acquisition, a data acquisition sequence, and the like are the same as those in the case shown in FIG. 3. However, this technique differs from that shown in FIG. 3 in that multislice dynamic (continuous) acquisition is performed asynchronously without using any electrocardiographic waveform.

In ECG-gated myocardial perfusion imaging described above, in consideration of a change in cardiac rate during imaging operation, the number of slices to be imaged must be reduced small enough to fall within the cardiac cycle measured before the imaging operation. For this reason, the number of slices that can be imaged is limited. In contrast, in this asynchronous myocardial perfusion imaging, imaging is performed asynchronously with respect to an electrocardiographic waveform. As shown in FIG. 7, therefore, there is no trigger wait time for an R wave before imaging operation in the next time phase, and the number of slices that can be imaged within a unit time can be increased. In addition, since data acquisition is always executed in a period of time determined by a pulse sequence length, dynamic time phases are always set at predetermined intervals.

Data in the respective dynamic time phases which are acquired in this asynchronous myocardial perfusion imaging differ from those obtained in ECG-gated myocardial perfusion imaging in that even the data of the same slice are images in different cardiac time phases.

Figure 8:
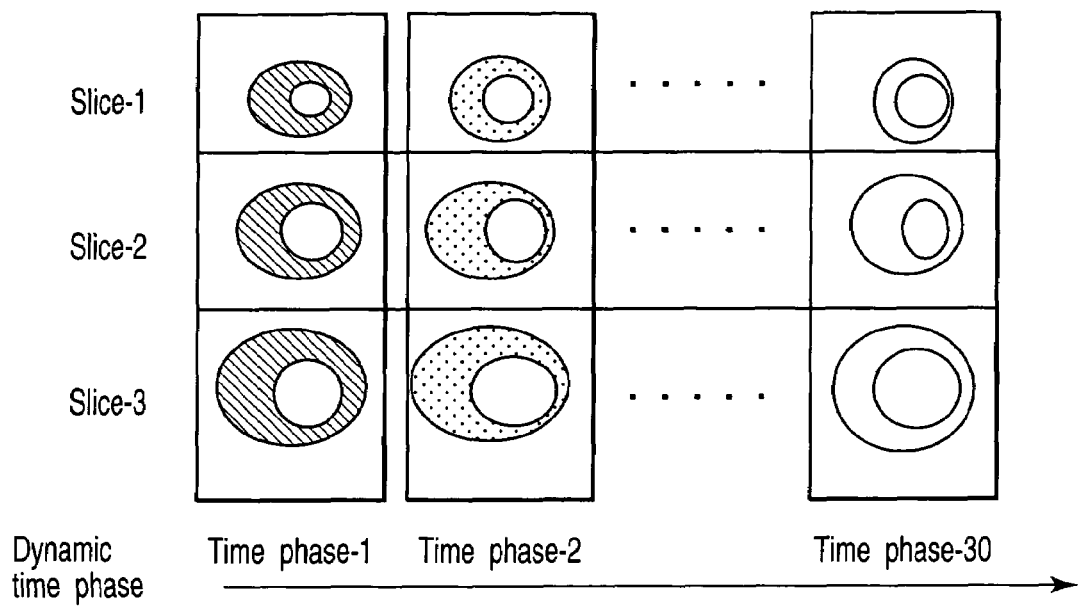
FIG. 8 is a view showing cross-sections (slices 1, 2, and 3) obtained in the respective dynamic time phases in accordance with the scan sequence shown in FIG. 7.

FIG. 8 is a view showing the respective cross-sections (slices 1, 2, and 3) obtained in the respective dynamic time phases in accordance with the scan sequence shown in FIG. 7. In the case shown in FIG. 8, three-slice imaging is repeated in 30 time phases to obtain 90 images. The image data obtained in this manner are reconstructed into MR images by the reconstruction unit 204 (step S22).

A Bull's eye image in each dynamic time phase is generated on the basis of each image obtained by asynchronous multislice dynamic imaging (step S23). That is, an endocardial and an epicardial contour are extracted from each cross-sectional image in each time phase. The region between the extracted endocardial and epicardial contour is divided into, for example, 100 radial regions (referring to FIG. 8, the region between the extracted endocardial and epicardial contour is divided into eight small regions, and the entire left ventricular cardiac muscle is divided into a total of 3×8=24 small regions as in the case shown in FIG. 4).

Figure 9:
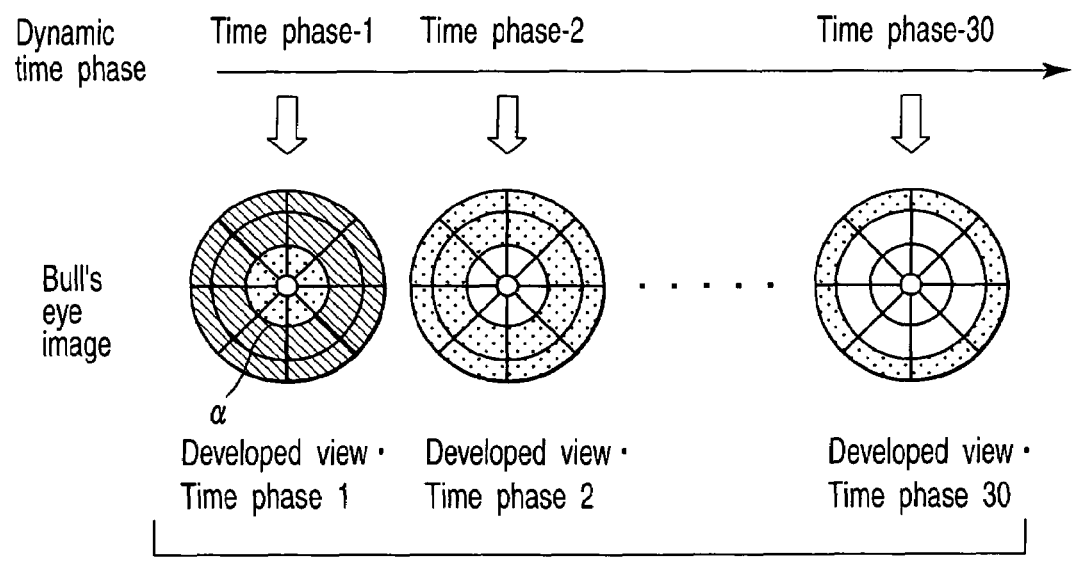
FIG. 9 is a view showing a Bull's eye image in each time phase on the basis of MR images obtained by asynchronous-multi slice dynamic imaging.

Specific values of the pixel values in the respective divided small regions are calculated and are associated with predetermined colors or grayscale values to generate a Bull's eye image as a developed view of the entire left ventricular cardiac muscle in each dynamic time phase, as shown in FIG. 9 (step S23). Note that, the specific value is an average value of the pixel values in the each small regions or a median value of pixel values in the each small region. In the following, the specific value of the pixel values in each small region is an average value of the pixel values in the small region to simplify the description.

Figure 10:
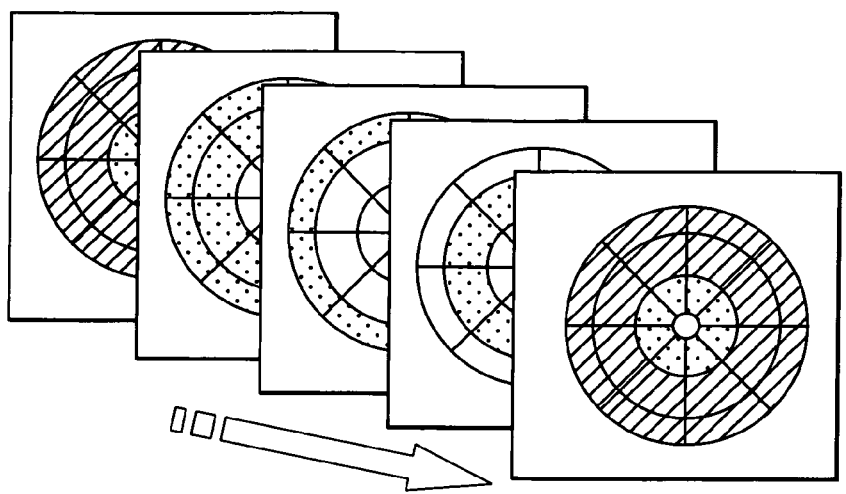
FIG. 10 is a view for explaining cine display of the Bull's eye images shown in FIG. 9.

Performing continuous moving image (cine) display of the generated Bull's eye images in the respective time phases in time phase order as shown in FIG. 10 makes it possible to visualize, as one image, changes in contrast medium distribution in the entire left ventricular cardiac muscle in the first circulation (step S24). That is, in ECG-gated myocardial perfusion imaging, a plurality of slice images need to be separately displayed as moving images, and hence it is difficult to observe the entire left ventricular hemodynamics at a glance. In contrast, according to this technique, as described above, since imaging is performed without using any ECG-gated technique, even the image data of the same slice are basically image data acquired in different cardiac time phases, and the shape of the cardiac muscle changes. However, the cardiac muscle of each image is divided into regions to generate developed views in step S23, and are continuously displayed in step S24. This technique therefore allows visual recognition of changes in pixel value unlike ECG-gated myocardial perfusion imaging.

Figure 11:
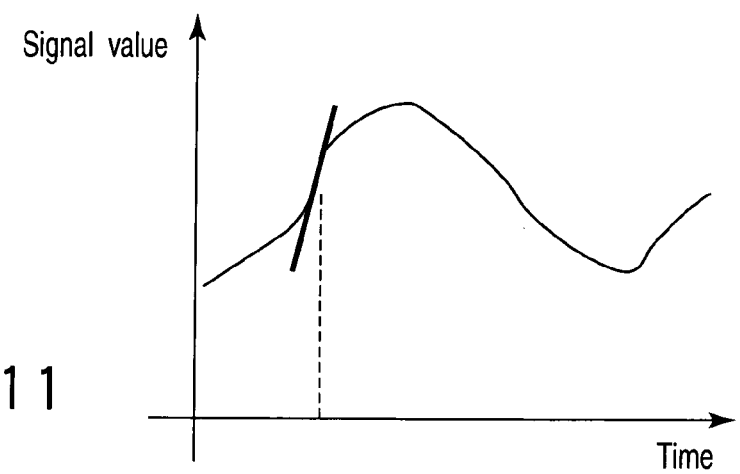
FIG. 11 is a view showing an example of a dynamic curve concerning a small region α of the cardiac muscle shown in FIG. 9.

Subsequently, dynamic curves representing temporal changes in signal value in the respective small regions of the cardiac muscle are generated from the obtained pixel values of Bull's eye images (developed views) in the respective dynamic time phases (step S25). FIG. 11 shows an example of a dynamic curve concerning a small region α of the cardiac muscle shown in FIG. 9. Obviously, there are a total of 3×8=24 dynamic curves corresponding to this small region and the remaining small regions.

Parameter values such as the maximum signal values in the respective regions, the maximum gradients, the times taken to reach the maximum gradients, and average signal values are calculated on the basis of the respective dynamic curves (step S26). Associating the calculated parameter values with colors or grayscale values makes it possible to generate a Bull's eye image (developed view) concerning each small region like that shown in FIG. 12 (step S27).

Figure 12:
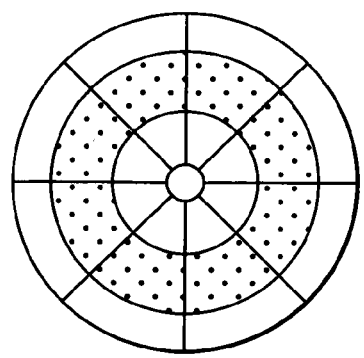
FIG. 12 is a view showing a Bull's eye image based on a dynamic curve obtained in asynchronous myocardial perfusion imaging.

Note that FIG. 12 shows an example of displaying the time taken to reach the maximum gradient of the dynamic curve in each region. The Bull's eye images obtained in step S27 provide information equivalent to those obtained in step S5.

The Bull's eye images generated in step S27 (the second Bull's eye images) are displayed with the Bull's eye images generated in step S23 (the first Bull's eye images) (step S28). In this case, a predetermined display form can be that the first Bull's eye image corresponding to a predetermined phase is displayed as a static image with the second Bull's eye image which is a static image, another predetermined display form can be that the first Bull's eye images are displayed time-serially (i.e. displayed cinematically), yet another predetermined display form can be that the first Bull's eye images are displayed simultaneously, etc.

According to the above arrangement, the following effects can be obtained.

According to this magnetic resonance imaging apparatus, multislice dynamic imaging is executed without using any ECG-gated technique, and diagnosis information concerning myocardial hemodynamics is generated on the basis of the execution of this imaging operation. Therefore, since no ECG-gated signal is required, there is no need to attach electrodes for electrocardiographic signal detection to the subject. In addition, there is no possibility of interruption in imaging operation due to a problem in an ECG-gated signal, a change in the cardiac rate of the subject during imaging operation, and the like. This makes it possible to omit operation of setting electrodes at proper positions and the like, thereby reducing the operational load on the operator, the physical load on the subject, and the like.

In addition, according this magnetic resonance imaging apparatus, since there is no need to attach electrodes to a subject to be examined, there is no possibility that the application of radio-frequency pulses for imaging will cause a burn and the like. This makes it possible to realize safe imaging operation and reduce the attention loads on the operator and the subject.

Furthermore, according to this magnetic resonance imaging apparatus, since no ECG-gated signal is required, gradient field switching noise which is a cause of a deterioration in image quality and an operation error can be prevented from being induced into an electrocardiographic waveform. If the data of a preset number of slices cannot be acquired within a planned cardiac cycle due to a problem in an ECG-gated signal, a change in the cardiac rate of the subject during imaging operation, and the like, the temporal resolutions of dynamic imaging become irregular intervals as a result of waiting for the next R wave. For this reason, a desired temporal resolution may not be obtained, resulting in inconveniences such as a deterioration in the reliability of diagnosis information in observation by cine display or dynamic analysis. In myocardial perfusion examination, imaging cannot be redone because of the use of a contrast medium. It is therefore necessary to avoid diagnosis failure due to interruption of imaging after the injection of a contrast medium or a deterioration in image quality as much as possible. This magnetic resonance imaging apparatus can eliminate all inconveniences caused by the ECG-gated technique, and hence can decrease the probability of redoing imaging operation and provide high-quality diagnosis information as compared with the prior art.

In addition, this magnetic resonance imaging apparatus executes multi slice dynamic imaging without using any ECG-gated technique, and generates diagnosis information concerning myocardial hemodynamics on the basis of the execution of this imaging operation. Bull's eye images directly obtained from MR images obtained by multi slice dynamic imaging and dynamic curves generated from the Bull's eye images can, in particular, be regarded as new diagnosis information which does not exist in the prior art. Therefore, this magnetic resonance imaging apparatus can provide new information effective for diagnosis, and can contribute to an improvement in the quality of medical practice.

Note that the present invention is not limited to the above embodiment, and constituent elements can be modified and embodied in the execution stage within the spirit and scope of the invention. The following are specific modifications of the embodiment.

(1) The respective functions according to this embodiment, and more particularly, the respective functions for executing asynchronous myocardial perfusion imaging can be implemented by, for example, installing programs for executing the functions in a computer such as a workstation and loading them in a memory. In this case, the programs which can make the computer implement this technique can be distributed while being stored in a recording medium such as a magnetic disk (a floppy disk or hard disk), an optical disk (e.g., a CD-ROM or DVD), or a semiconductor memory.

(2) The above embodiment has been exemplified as a magnetic resonance imaging apparatus including the imaging system. However, the imaging system is not necessarily essential. For example, the present invention can also be realized by a magnetic resonance data processing apparatus (image processing apparatus) which stores, in advance, image data (which is not limited to data before or after image reconstruction) obtained by, for example, asynchronous multislice dynamic imaging and can execute post-processing and display in asynchronous myocardial perfusion imaging.

(3) The above embodiment has been exemplified as a scan sequence shown in FIG. 7 and FIG. 7 in which three-slice imaging is repeated in 30 time phases to obtain 90 images. However, the slices number n acquired in one multi slice scan and the time phases number m in which the multi slice scan is repeated are not limited to the above description. The slices number n acquired in one multi slice scan and the time phases number m in which the multi slice scan is repeated may be set at an arbitrary natural number more than one.

In addition, various modifications can be formed by proper combinations of a plurality of constituent elements disclosed in the above embodiment. For example, several constituent elements may be omitted from all the constituent elements disclosed in the above embodiment. Furthermore, constituent elements in different embodiments may be properly combined.

What is claimed is:

1. A magnetic resonance imaging apparatus comprising:
an imaging unit which repeatedly executes a multi-slice imaging operation by repeatedly applying a gradient field and a radio-frequency pulse to a subject to be examiner which is place in a static field space and receiving magnetic signals generated in respectively corresponding slice-volumes of the heart of the subject by application of the slice-selecting gradient field and radio-frequency pulse asynchronously with respect to cardiac cycles of said heart;
a control unit which controls the imaging unit so as to sequentially change the frequency of the radio-frequency pulse and/or the magnitude of the gradient field so as to achieve repeated multi-slice imaging sequences each repetition of the multi-slice sequence constituting a respectively corresponding dynamic time phase containing one complete multi-slice imaging operation;
an imaging reconstruction unit which executes image reconstruction by using magnetic resonance signals received by the multi-slice imaging sequences and obtains a plurality of first images of the heart for each dynamic time phase providing a plurality of slice-volume cross-sections;

a processing unit which divides the heart of the subject in the first image in the same dynamic time phase into a plurality of small regions and generates a specific value for each of each pixel values in each said small region of the image of the heart;

an image generating unit which generates a first Bull's eye view in a dynamic time phase, the first Bull's eye view providing a Bull's eye two-dimensional developed views of the heart for visualizing a function of each said small region of the heart according to the specific values; and a display unit which displays the first Bull's eye view for each dynamic time phase in a predetermined form.

2. An apparatus according to claim 1, wherein a specific value in each said small region is an average of pixel values in such small region or a median of pixel values in such small region.

3. An apparatus according to claim 1, further comprising a diagnosis information generating unit which generates diagnosis information based on the first Bull's eye (developed) view for each dynamic time phase.

4. An apparatus according to claim 3, wherein the diagnosis information generating unit generates a temporal change in the specific value in at least one of the plurality of small regions on the basis of the first Bull's eye (developed) view for each dynamic time phase.

5. An apparatus according to claim 4, wherein the diagnosis information generating unit generates a dynamic curve with respect to at least one of the plurality of small regions on the basis of the temporal change in the specific value.

6. An apparatus according to claim 1, wherein the diagnosis information generating unit generates temporal change in the specific value in each said small region on the basis of the first Bull's eye (developed) view for each dynamic time phase, calculates characteristic values in each said small region on the basis of the temporal change and generates a second Bull's eye (developed) view representing the characteristic values in each said small region for each dynamic time phase.

7. An apparatus according to claim 6, wherein the characteristic value is a maximum pixel value, an average of pixel values, the maximum gradient of a dynamic curve representing a temporal change of the specific value with respect to at least one of the plurality of small regions or the time taken to reach the maximum gradient.

8. An apparatus according to claim 6, wherein the display unit continuously displays the first developed views in respective dynamic time phases in a time-ordered series.

9. An apparatus according to claim 1, wherein the multi-slice images obtained in one dynamic time phase are all obtained within a period of time that is equal to or less than the subject's cardiac cycle period as measured before the multi-slice imaging operations are performed.

10. A magnetic resonance data processing apparatus comprising:

a storage unit which stores magnetic resonance data obtained by acquiring magnetic resonance signals generated in the heart of a subject to be examined by repeated multi-slice imaging operations conducted asynchronously with respect to cardiac cycles of said heart so as to achieve repeated multi-slice imaging sequences, each repetition of the multi-slice sequence constituting a respectively corresponding dynamic time phase of a complete set of multi-slice imaging operations;

an image reconstruction unit which executes image reconstruction by using the magnetic resonance data and obtaining a plurality of first images for each dynamic time phase of said repeated multi-slice imaging operations with respect to a plurality of slice-volume cross-sections;

an image generating unit which generates a first Bull's eye (developed) view having a specific value in each of plural small multi-pixel regions thereof obtained when the heart of the subject in the first Bull's eye images in the same dynamic time phase is developed by being divided into a plurality of small multi-pixel regions; and a display unit which displays the first Bull's eye (developed) view for each dynamic time phase in a predetermined form.

11. A magnetic resonance imaging apparatus control method comprising:

executing multi-slice image reconstruction using magnetic resonance data obtained by acquiring magnetic resonance signals generated in the heart of a subject to be examined by repetitively performing multi-slice imaging operations asynchronously with respect to cardiac cycles of said heart so as to achieve repeated multi-slice imaging sequences, each repetition of the multi-slice sequence constituting a respectively corresponding dynamic time phase of a complete set of multi-slice imaging operations, thereby obtaining a plurality of first images for each dynamic time phase of said repeated multi-slice imaging operations with respect to a plurality of respectively corresponding slice-volume cross-sections asynchronously with respect to cardiac cycles of said heart;

dividing the image of the heart of the subject in the first images in the same dynamic time phase into a plurality of small multi-pixel regions and generating a first Bull's eye (developed) view representing a specific value in each said small region obtained for each dynamic time phase; and displaying the first Bull's eye view for each dynamic time phase in a predetermined form on a display unit.

12. A control method according to claim 11, wherein the specific value in each said small region is an average of pixel values in such small region or a median of pixel values in such small region.

13. A control method according to claim 11, further comprising generating diagnosis information based on the first developed view for each dynamic time phase.

14. A control method according to claim 11, further comprising generating a temporal change in the specific value in at least one of the plurality of small regions on the basis of the first developed view for each dynamic time phase.

15. A control method according to claim 14, further comprising generating a dynamic curve with respect to at least one of the plurality of small regions on the basis of a temporal change in the specific value.

16. A control method according to claim 11, further comprising:

generating temporal change in the specific value in the each small region on the basis of the first Bull's eye (developed) view for each dynamic time phase;

calculating characteristic values in each small region on the basis of the temporal change; and generating a second Bull's eye (developed) view representing the characteristic values in each small region for each dynamic time phase.

17. A control method according to claim 16, wherein the characteristic value is a maximum pixel value, an average of pixel values, the maximum gradient of the dynamic curve representing a temporal change of the specific value with respect to at least one of the plurality of small regions or the time taken to reach the maximum gradient.

18. A control method according to claim 17, further comprising displaying the first Bull's eye (developed) views in the respective dynamic time phases continuously in time-ordered series.

19. A magnetic resonance imaging apparatus control method comprising:
   executing multi-slice image reconstruction using magnetic resonance data obtained by acquiring magnetic resonance signals generated in the heart of a subject to be examined by repetitively performing multi-slice imaging operations asynchronously with respect to cardiac cycles of said heart so as to achieve repeated multi-slice imaging sequences, each repetition of the multi-slice sequence constituting a respectively corresponding dynamic time phase of a complete set of multi-slice imaging operations, thereby obtaining a plurality of respectively corresponding first slice-volume images for each dynamic time phase of said repeated multi-slice imaging operations with respect to a plurality of slice-volume cross-sections; and
   dividing the heart image of the subject in the first images in the same dynamic time phase into a plurality of small multi-pixel regions and generating a first Bull's eye (developed) view representing a specific value in each said small region obtained for each dynamic time phase; and
   displaying the first Bull's eye view for each dynamic time phase in a predetermined form on a display unit.

20. A magnetic resonance imaging apparatus comprising:
   an imaging unit which repeatedly executes multi-slice imaging operations asynchronously with respect to cardiac cycles of said heart so as to achieve repeated multi-slice imaging sequences, each repetition of the multi-slice sequence constituting a respectively corresponding dynamic time phase of a complete set of multi-slice imaging operations;
   an image reconstruction unit which executes image reconstruction by using the magnetic resonance signals received by the repeated multi-slice imaging operations and thereby obtains a plurality of first images for each dynamic time phase of said repeated multi-slice imaging operations with respect to a plurality of slice-volume cross-sections;
   an image generating unit which divides the heart image of the subject in the first images in the same dynamic time phase into a plurality of small multi-pixel regions and generates a first Bull's eye (developed) view representing an average value in each said small region or a median of pixel values in such small region for each dynamic time phase; and
   a display unit which displays the first Bull's eye (developed) view for each dynamic time phase in a predetermined form.

* * * * *